(12) United States Patent
Lee

(10) Patent No.: US 10,705,021 B2
(45) Date of Patent: Jul. 7, 2020

(54) METHOD FOR MANUFACTURING BIOCHIP HAVING IMPROVED FLUORESCENT SIGNAL SENSING PROPERTIES AND BIOCHIP MANUFACTURED BY THE SAME

(71) Applicant: OPTOLANE TECHNOLOGIES INC., Seongnam-si, Gyeonggi-do (KR)

(72) Inventor: Do Young Lee, Seongnam-si (KR)

(73) Assignee: OPTOLANE TECHNOLOGIES INC., Seongnam-si, Gyeonggi-Do (KR)

(*) Notice: Subject to any disclaimer, the term of this patent is extended or adjusted under 35 U.S.C. 154(b) by 204 days.

(21) Appl. No.: 15/855,013

(22) Filed: Dec. 27, 2017

(65) Prior Publication Data

US 2018/0136127 A1    May 17, 2018

Related U.S. Application Data

(62) Division of application No. 14/863,511, filed on Sep. 24, 2015, now Pat. No. 9,885,658.

(30) Foreign Application Priority Data

Sep. 25, 2014  (KR) .................. 10-2014-0128466
Sep. 8, 2015   (KR) .................. 10-2015-0126756

(51) Int. Cl.
| | | |
|---|---|---|
| G01N 21/64 | (2006.01) | |
| H01L 27/146 | (2006.01) | |
| C12Q 1/6837 | (2018.01) | |
| H01L 27/14 | (2006.01) | |
| G01N 33/53 | (2006.01) | |
| B01L 3/00 | (2006.01) | |

(52) U.S. Cl.
CPC ....... *G01N 21/6428* (2013.01); *C12Q 1/6837* (2013.01); *G01N 21/6454* (2013.01); *G01N 21/6456* (2013.01); *G01N 21/6458* (2013.01); *G01N 21/6486* (2013.01); *G01N 33/5304* (2013.01); *H01L 27/14* (2013.01); *H01L 27/14621* (2013.01); *H01L 27/14625* (2013.01); *H01L 27/14685* (2013.01); *H01L 27/14687* (2013.01); *B01L 3/5027* (2013.01); *G01N 2201/062* (2013.01)

(58) Field of Classification Search
None
See application file for complete search history.

(56) References Cited

U.S. PATENT DOCUMENTS

2005/0236553 A1* 10/2005 Noto ................ H01L 27/14621
250/208.1

* cited by examiner

*Primary Examiner* — Neil N Turk
(74) *Attorney, Agent, or Firm* — Kile Park Reed & Houttleman PLLC

(57) ABSTRACT

Provided is a biochip having improved fluorescent signal sensing properties. A filter layer is provided between a bio-layer and a light sensor layer so as to remove noise generated by stray light during a bio-reaction process. Thereby, the sensitivity of the light sensor layer can be enhanced.

10 Claims, 21 Drawing Sheets

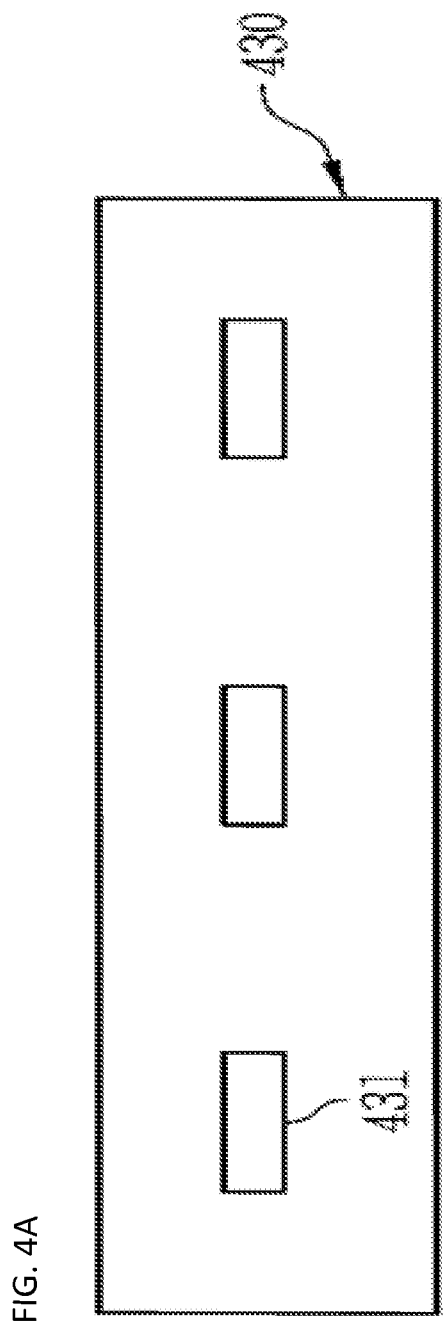

METHOD FOR MANUFACTURING BIOCHIP HAVING IMPROVED FLUORESCENT SIGNAL SENSING PROPERTIES AND BIOCHIP MANUFACTURED BY THE SAME

CROSS REFERENCE TO RELATED APPLICATIONS

This application is a divisional application of U.S. patent application Ser. No. 14/863,511, filed Sep. 24, 2015 (currently pending), the disclosure of which is herein incorporated by reference in its entirety. The U.S. patent application Ser. No. 14/863,511 claims priority from and the benefit of Korean Patent Application No. 10-2014-0128466 filed Sep. 25, 2014, and Korean Patent Application No. 10-2015-0126756 filed Sep. 8, 2015, which are hereby incorporated by reference for all purposes as if fully set forth herein.

BACKGROUND

1. Technical Field

Exemplary embodiments of the present disclosure relates to a method for manufacturing biochips and a biochip manufactured by the method, and more particularly, to a method for manufacturing a biochip having improved fluorescent signal sensing properties which can provide a location-based multi-sensing function and be applied to a realtime quantitative PCR (polymer chain reaction), and a biochip manufactured by the manufacturing method.

2. Related Art

Generally, a biochip is formed by regularly arranging reference samples including biological material such as DNA or proteins on a substrate made of material such as glass, metal such as gold, or nylon.

The biochip basically uses biochemical reactions between the reference sample fixed to the substrate and a target sample. Representative examples of the biochemical reaction between the reference sample and the target sample include the complementary binding of DNA bases, an antigen-antibody immune reaction and so forth.

Optical-based quantitative and qualitative diagnosis using the biochip is generally performed by detecting the degree of a biochemical reaction between the reference sample and the target sample through a process in which a result product of the biochemical reaction is converted into detectable light. Optical conversion media which are generally used are based on color formation, chemiluminescence, fluorescence, etc. resulting from chemical combination.

FIG. 1 is a view illustrating a conventional fluorescent reaction detection system.

Referring to FIG. 1, the conventional fluorescent reaction detection system includes a light source 10, a band-pass filter 20, a biochemical reaction device 30, a fluorescent band-pass filter 40 and a light sensing device 50 which are separated from each other.

When the distance between the biochemical reaction device 30 in which a biochemical reaction takes place and the light sensing device 50 is denoted by R and a radius of an opening of a light sensor in the light sensing device 50 is denoted by r, the quantity of fluorescent light that is incident on the light sensor, compared to the total quantity (I) of fluorescent light generated as the result of the biochemical reaction, is reduced to $I(\pi r2)/(4\pi R2)$ with loss of a lot of light signals.

Therefore, if the ratio of r/R is reduced, the quantity of light that is incident on the light sensor is reduced, whereby the sensitivity is reduced. As the ratio of r/R approaches 1, the sensitivity becomes increased. To maximize the sensitivity, there is the need for embodying the system such that the light sensor and the location of the bio-reaction region are as close to each other as possible.

FIG. 2 is a sectional view of a biochip provided with a light sensor so as to solve the above-mentioned conventional problem.

Referring to FIG. 2, the conventional biochip 100 provided with a light sensor includes a bio-layer 110 and a light sensor layer 120.

The bio-layer 110 includes a reaction region 111 in which a biochemical reaction between a reference sample 111a and a target sample 111b takes place. Furthermore, to make it possible to determine a result of the biochemical reaction, the bio-layer 110 is embodied in such a way that luminescent or fluorescent material remains in the reaction region 111 depending on the degree of reaction.

In the case where luminescent material remains, there is no need for a separate light source because external environment has only to be formed such that the luminescent material itself emits light. However, in the case where fluorescent material remains, a separate light source is required to excite the fluorescent material.

For this, the conventional technique uses the following method: a separate external light source and a fluorescent band-pass filter are provided on an upper end of the optical sensor, or a light emitting device 112 having a reflective plate 113 in a lower portion thereof is installed in the bio-layer 110, so that light emitted from the light emitting device is used to excite the fluorescent material in the bio-layer.

However, in the conventional biochip, while fluorescent signals are created as a result of a biochemical reaction by means of light emitted from the external light source and the internal light emitting device, noise signals of an excitation light that reach thousands to tens of thousands of times more than the fluorescent signals are also generated. Such noise signals enter the light sensor layer, thus making it difficult to correctly detect fluorescent signals resulting from the biochemical reaction.

SUMMARY

Various embodiments are directed to a method for manufacturing a biochip having improved fluorescent signal sensing properties and a biochip manufactured by the method, in which: a light emitting device provided with a metal wiring layer under a lower portion thereof is formed in a biochip to excite fluorescent material; a fluorescent-excitation-light band-reject-filter layer for blocking excitation light required for fluorescence is separately formed in a boundary between a bio-layer and a light sensor layer; and a color filter layer is formed on an upper surface of the light sensor layer to block excitation light and allow fluorescent signals to pass therethrough depending on a band of wavelength of the fluorescent material, whereby excitation light noise generated from the bio-layer can be blocked as much as possible from being incident on the light sensor layer, thus making it possible to detect more minute fluorescent signals.

In an embodiment, a method for manufacturing a biochip having improved fluorescent signal sensing properties includes: forming a light sensor layer including a plurality of light sensing units, on a semiconductor substrate; planarizing a surface of the light sensor layer; forming a filter layer over the planarized light sensor layer; and forming a bio-layer over the filter layer, the bio-layer having a plurality of reaction regions in each of which a biochemical reaction between a reference sample and a target sample takes place, with light emitting devices embedded in the bio-layer, wherein light emitted from each of the light emitting devices is blocked from being incident on the corresponding light sensing unit.

In another embodiment, a biochip having improved fluorescent signal sensing properties includes: a bio-layer embedded with light emitting devices each of which has a metal wiring layer lying thereunder, and formed with a plurality of reaction regions in each of which a biochemical reaction between a reference sample and a target sample takes place; a filter layer formed under the bio-layer; and a light sensor layer which is formed under the filter layer, and in which a plurality of light sensing units are formed, wherein the filter layer is formed by planarizing an upper portion of the light sensor layer and stacking nanoscale thin films through an atomic layer deposition (ALD) process, and light emitted from each of the light emitting devices is blocked from being incident on the corresponding light sensing unit.

BRIEF DESCRIPTION OF THE DRAWINGS

FIGS. 4A to 4D are sectional views corresponding to the flowchart of the biochip manufacturing method according to the present disclosure;

DETAILED DESCRIPTION

Figure 1:
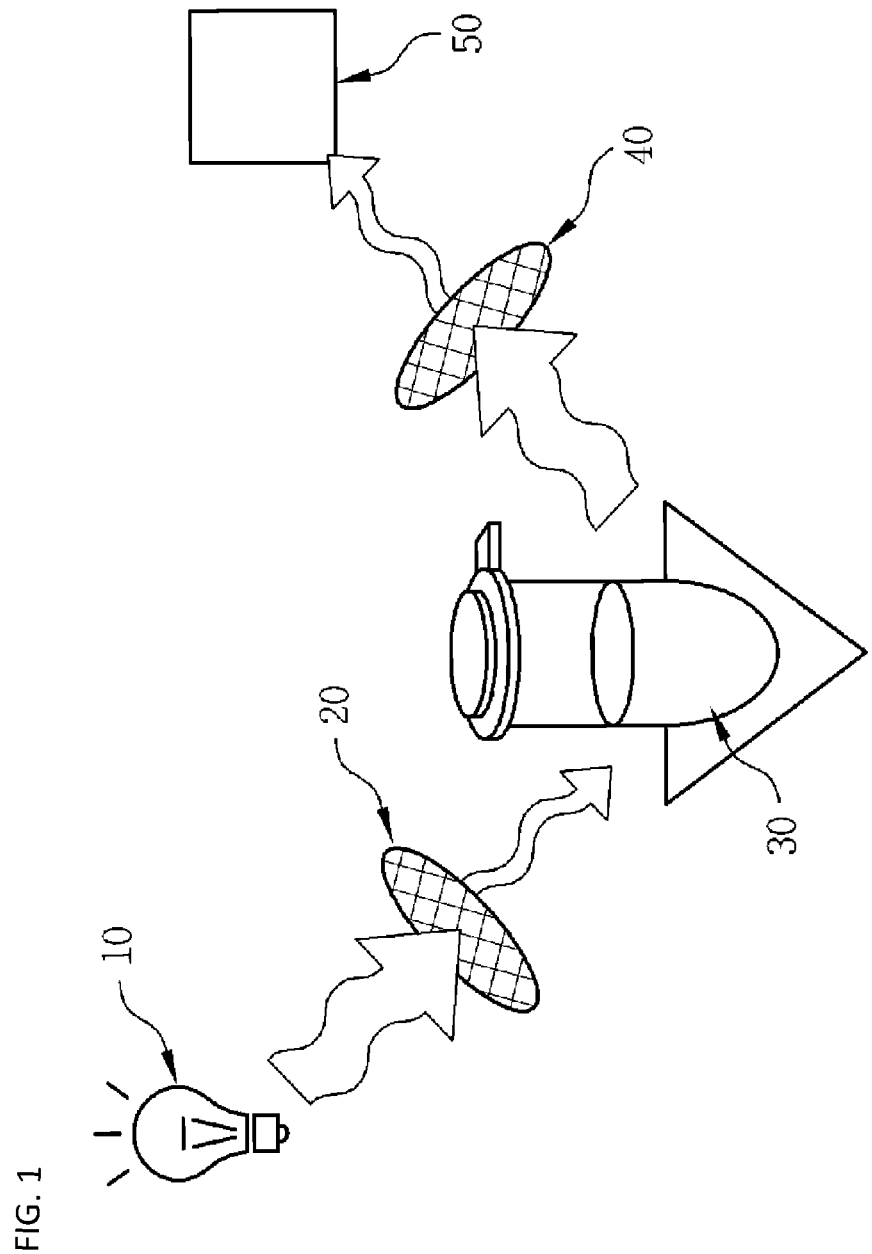
FIG. 1 is a view showing a typical fluorescent reaction detection system.
Figure 2:
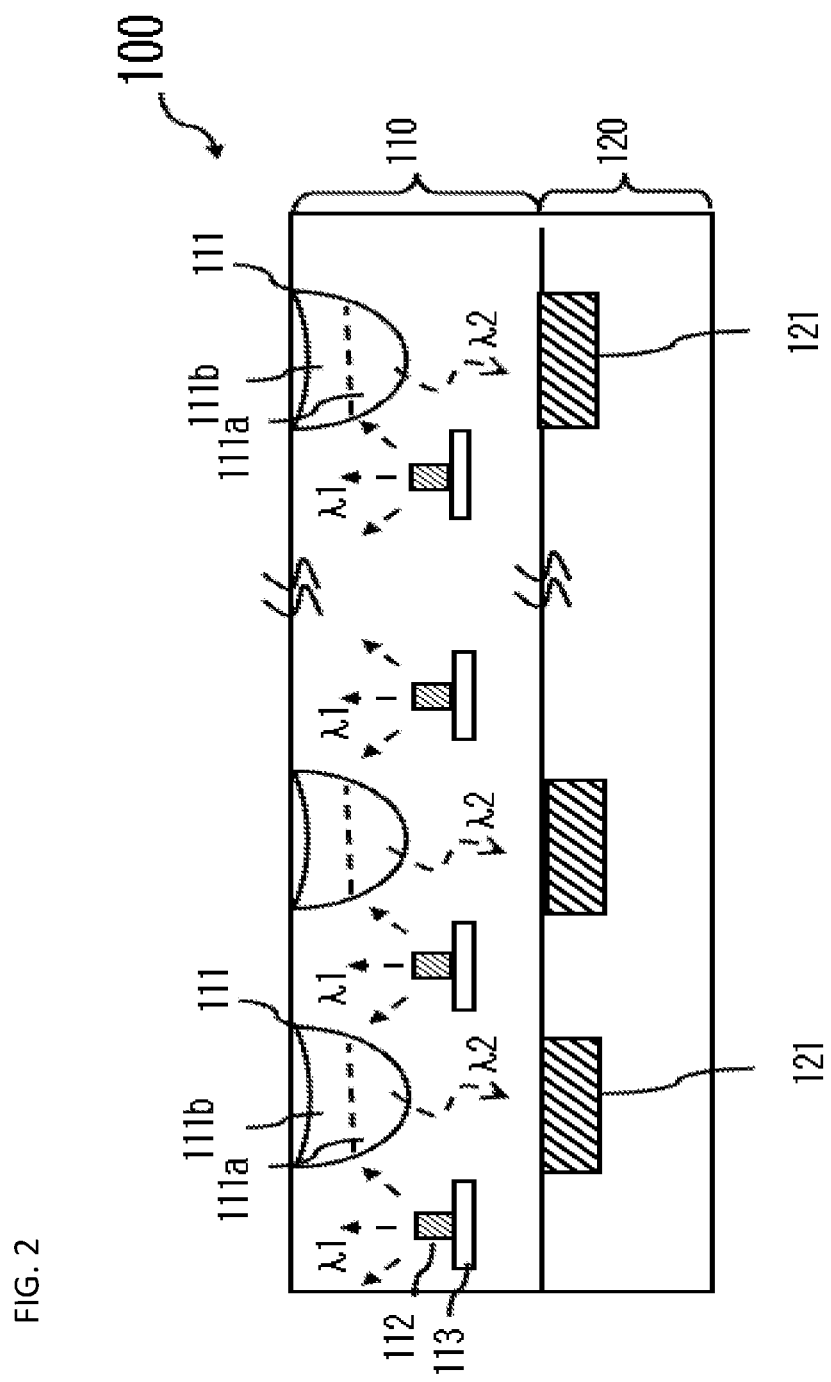
FIG. 2 is a sectional view of a biochip provided with a conventional light sensor.

Various embodiments will be described below in more detail with reference to the accompanying drawings. The present disclosure may, however, be embodied in different forms and should not be construed as limited to the embodiments set forth herein. Rather, these embodiments are provided so that this disclosure will be thorough and complete, and will fully convey the scope of the present disclosure to those skilled in the art. Throughout the disclosure, like reference numerals refer to like parts throughout the various figures and embodiments of the present disclosure.

Hereinafter, exemplary embodiments of the present disclosure will be described in detail with reference to the accompanying drawings.

Figure 3:
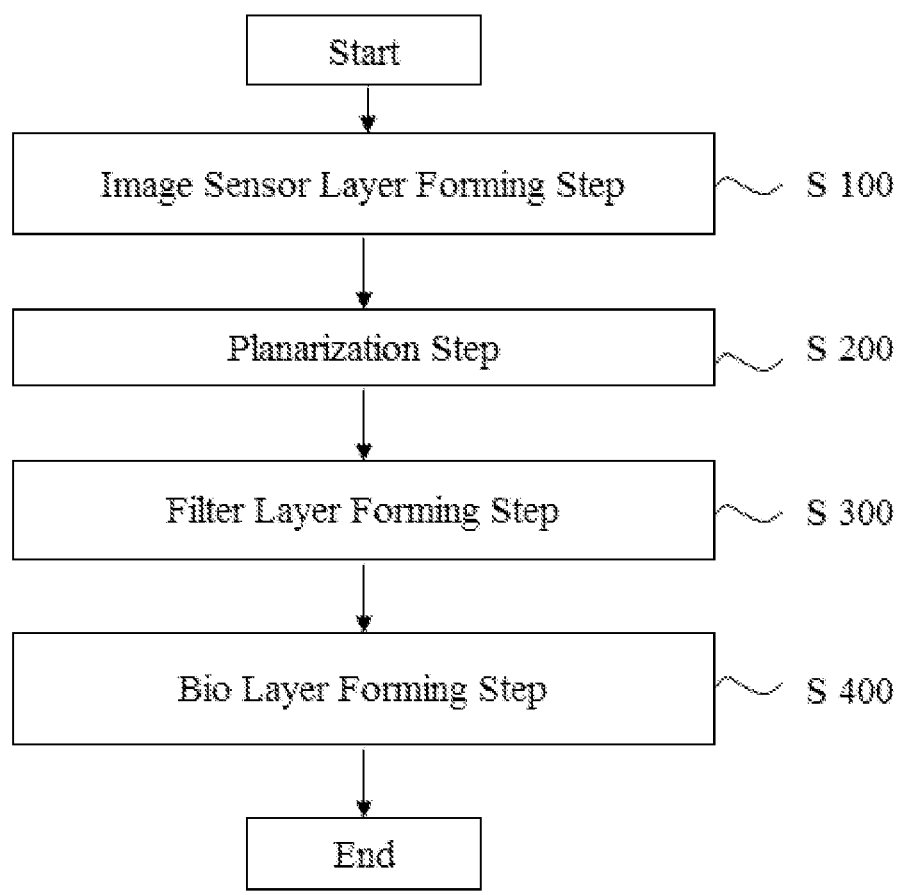
FIG. 3 is a flowchart of a method of manufacturing a biochip having improved fluorescent signal sensing properties according to the present disclosure

FIG. 3 is a flowchart of a method for manufacturing a biochip having improved sensing properties according to the present disclosure. FIGS. 4A to 4D are sectional views corresponding to the flowchart of the manufacturing method according to the present disclosure.

Referring to FIGS. 3 and 4, the biochip manufacturing method according to the present disclosure includes a light-sensor-layer forming step S100, a planarization step S200, a filter-layer forming step S300 and a bio-layer forming step S400.

At the light-sensor-layer forming step S100, a plurality of light sensing units are provided on a semiconductor substrate, thus forming a light sensor layer 430 (refer to FIG. 4A).

It is preferable that a photodiode be used as each of the light sensing units 431. Furthermore, to ensure reliable operation of a fluorescent sensing system of the present disclosure and increase a sensing range, photodiodes having different sizes are combined in a photodiode array.

Meanwhile, taking a light penetration depth of a light source into account, a depth to which each photodiode is disposed is preferably adjusted. In this way, a filtering function can be complemented.

That is, at the light-sensor-layer forming step, the depth to which the light sensing units are embedded can be adjusted taking the light penetration depth of the light source into account such that light emitted from a fluorescent excitation source, in other words, a light emitting device, can be blocked and most fluorescent light generated by bio-reaction can be absorbed. Thereby, the filtering function can be complemented.

Typically, a blue-based light source is used as a light emitting device that is used for bio-reactions. As such, in the case where the blue light source is used, each light sensing unit is preferably embedded in the semiconductor substrate to a depth ranging from 0.2 µm to 0.4 µm from the surface of the substrate so that the sensitivity of the light sensing unit can be enhanced.

At the light-sensor-layer forming step S100, an image signal processor (hereinafter, referred to as an 'ISP') which processes signals generated before and after a fluorescent reaction in the light sensor layer and thus is able to obtain a signal resulting from the fluorescent reaction may be further provided. The detailed operation of the ISP will be described later herein.

Figure 4B:
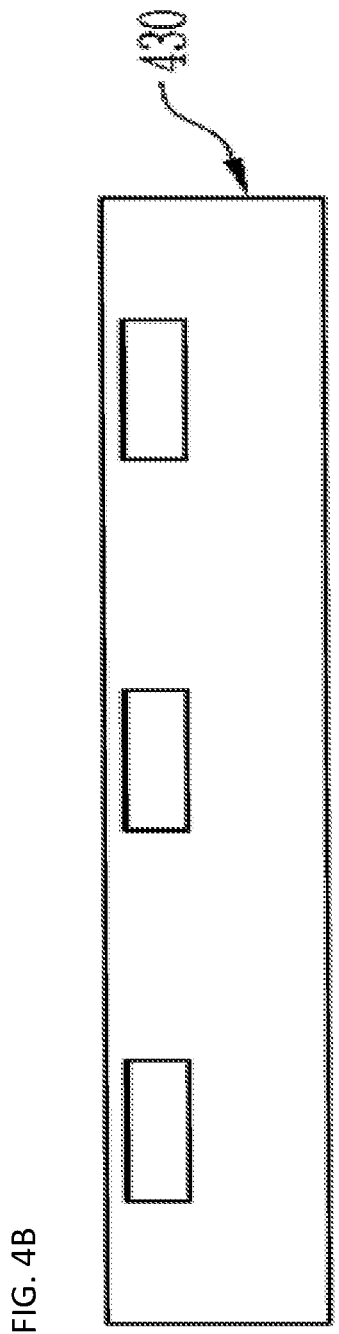

At the planarization step S200, an upper portion of the light sensor layer 430 is planarized (refer to FIG. 4B).

The upper surface of the light sensor layer 430 just after has been formed is generally uneven and has scratches rather. The reason for this is because of penetration of impurities or a chemical reaction induced during a semiconductor manufacturing process. When, as in the present disclosure, one or more layers of nanoscale thin films are formed on a desired surface, if the surface is uneven or scratched, it will not be easy to correctly deposit the thin films on the uneven or scratched surface. Thereby, the geometrical structure of the filter layer may become abnormal, whereby filtering characteristics of the filter layer may deteriorate. In addition, even if several tens of filter layers are formed by depositing, e.g., sixteen to forty layers of thin films, this problem is not solved but it is accumulated on each filter layer.

Therefore, before the filter layer 420 is formed on the upper surface of the light sensor layer 430, an operation of planarizing a target surface to be coated with the filter layer 420 is necessarily required.

Although a planarization operation for a typical semiconductor manufacturing process is for reliable formation of an upper structure, the planarization operation in the present disclosure is needed for preventing the quality of light reaching the light sensor layer from deteriorating. Furthermore, the planarization operation makes the filter layer 420 be more reliably formed on the even surface.

Here, the planarization operation can be performed by chemical-mechanical polishing (CMP).

Although a front side illumination (FSI) image sensor is illustrated in FIG. 4, the present disclosure may be applied to a back side illumination (BSI) image sensor, of course.

In the case of the FSI image sensor, a metal layer is present below a surface to be coated with the filter layer. Due to this, during the planarization operation, electrical uniformity may be broken, and it is not easy to control it. However, in the case of the BSI image sensor, there is no metal layer under a surface to be coated with the filter layer. Thus, a thin film can be directly deposited on a silicon substrate, so that there is no problem caused by a metal layer during the planarization operation. Therefore, in terms of performing the planarization operation, it is more preferable that the BSI image sensor be used.

Figure 4C:
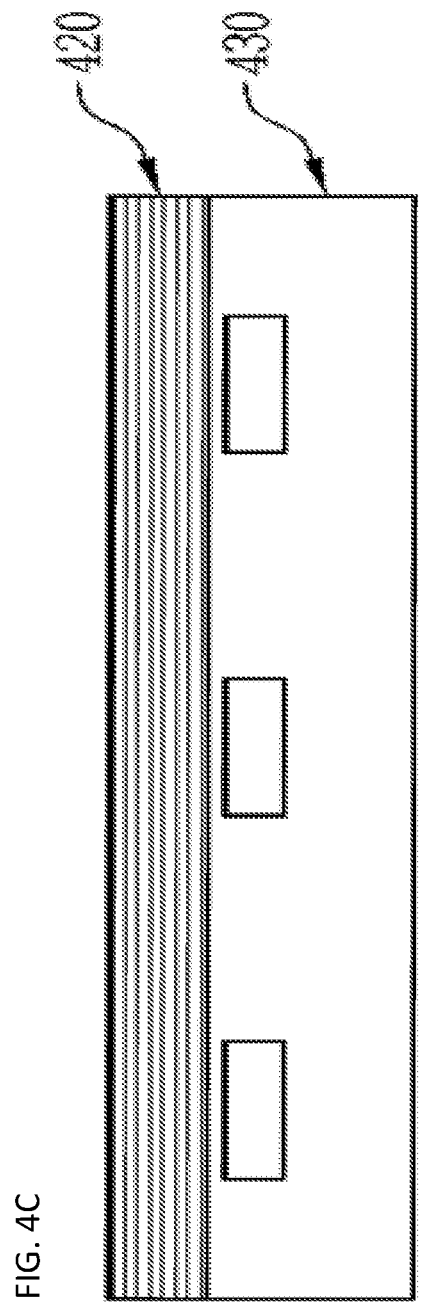

Thereafter, at the filter layer forming step S300, the filter layer 420 is formed on an upper surface of the planarized light sensor layer 430 (refer to FIG. 4C).

Although most light emitted from each light emitting device 412 provided in a bio-layer 410 is blocked by a metal wiring layer 413 and thus prevented from being incident on the light sensor layer 430, some of the light may being incident on the light sensor layer 430.

Furthermore, some light that is emitted from the light emitting device 412 and enters a reaction region 411 in which bio-reaction takes place may be reflected by the reaction region 411 and then be incident on the light sensor layer 430.

Such undesirable light that is incident on the light sensor layer 430 acts as noise, thus reducing the sensitivity of the image sensor.

To prevent a reduction in sensitivity of the image sensor, it is required for forming the filter layer 420 which can block undesirable light from being incident on the light sensor layer 430. Moreover, it is very important to adjust the thickness of the filter layer 420 so that a desired filter characteristic curve can be obtained.

The filter layer 420 may be formed through a single deposition process using a chemical vapor deposition (CVD) or physical vapor deposition (PVD) method. However, in this case, there are problems in that the quality of the formed film is uneven, and the sensitivity of the sensor cannot be ensured to a predetermined level or more.

Therefore, it is more preferable that the filter layer be formed by an atomic layer deposition (ALD) method in such a way that sixteen to forty layers of nanoscale thin films such as oxide films or nitride films are deposited one by one.

Figure 5:
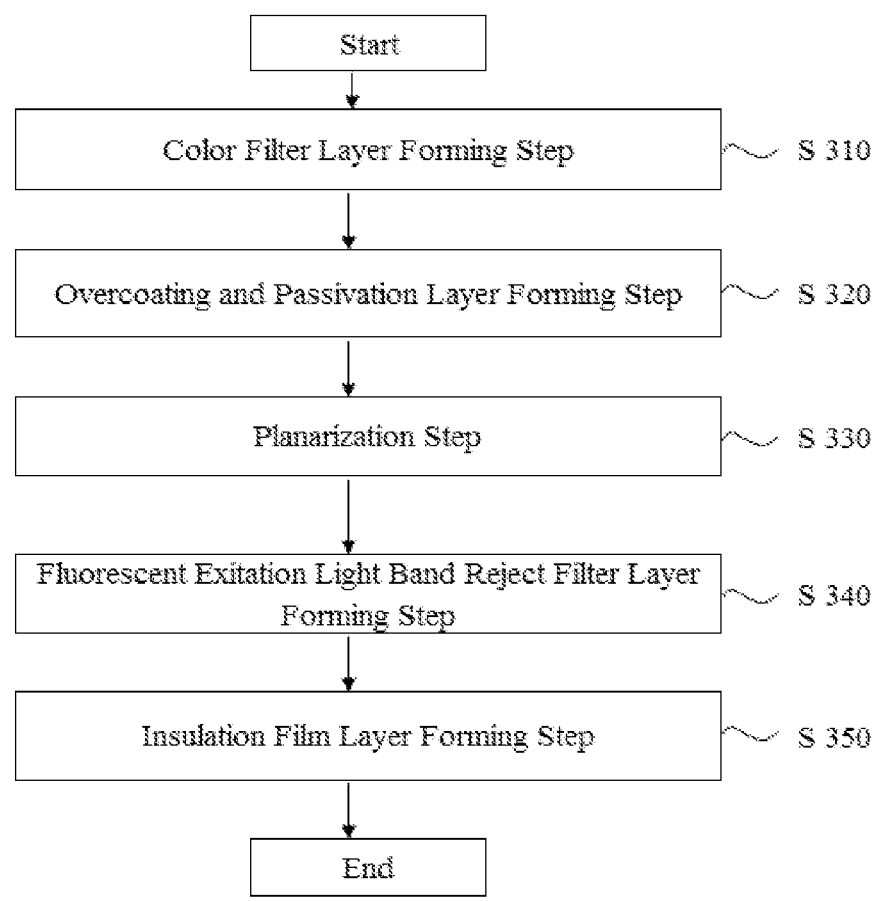
FIG. 5 is a flowchart showing a detailed process of a filter layer forming step of the biochip manufacturing method according to the present disclosure.
Figure 6:
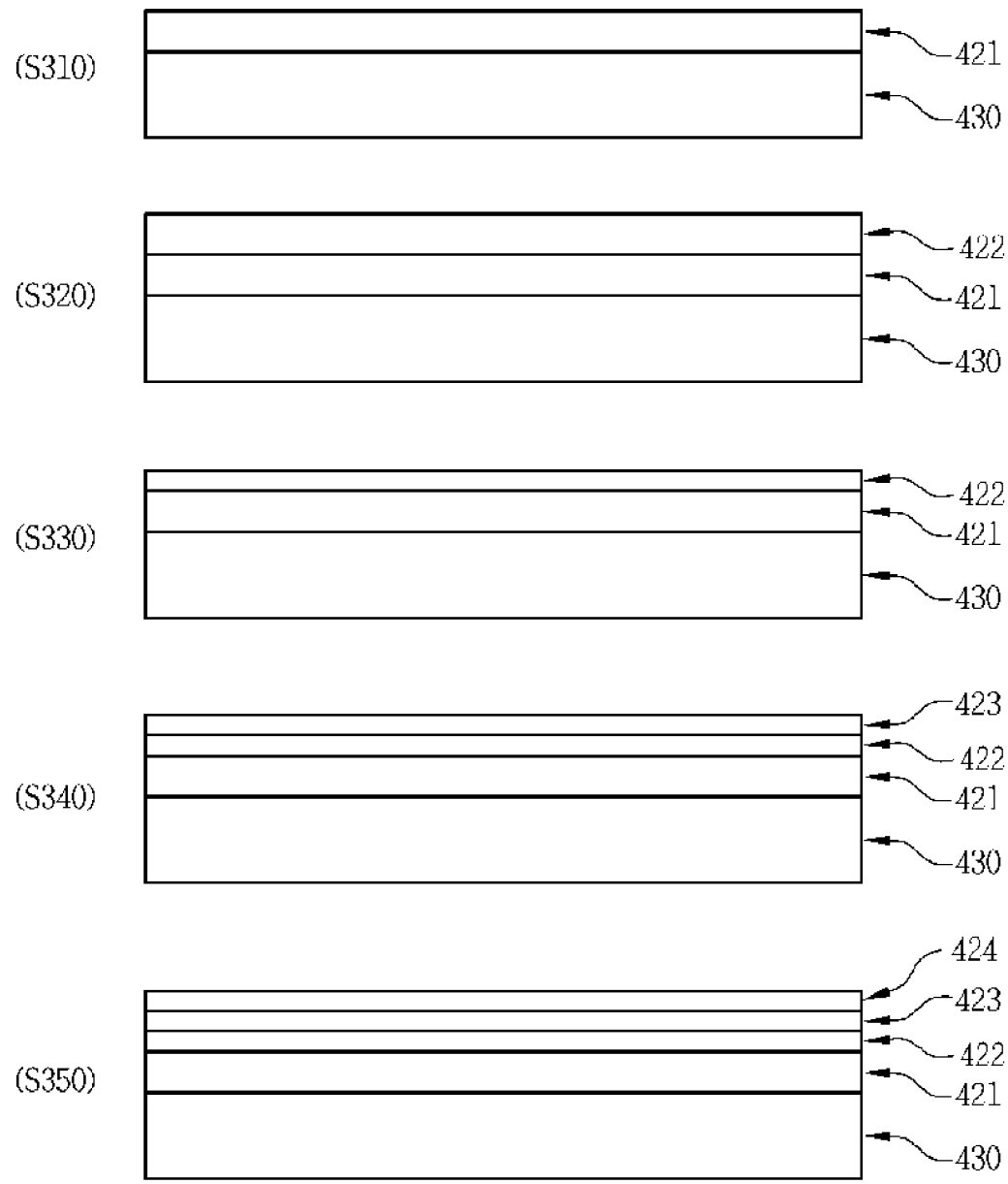
FIG. 6 shows sectional views corresponding to the flowchart of the detailed process of the filter layer forming step of the biochip manufacturing method according to the present disclosure.

FIG. 5 is a flowchart showing a detailed process of the filter layer forming step of the biochip manufacturing method according to the present disclosure. FIG. 6 shows sectional views corresponding to the flowchart of the detailed process of the filter layer forming step of the biochip manufacturing method according to the present disclosure.

Referring to FIGS. 5 and 6, the filter layer forming step S300 includes a color-filter-layer forming step S310, an overcoating and passivation layer forming step S320, a planarization step S330, a fluorescent-excitation-light band-reject-filter layer forming step S340 and an insulation-film-layer forming step S350.

At the color-filter-layer forming step S310, a color filter layer 421 which allows a fluorescence-band signal generated by bio-reaction to penetrate therethrough while blocking a fluorescent-excitation-light-band signal is formed.

Subsequently, an overcoating and passivation layer 422 for protecting a circuit is formed on the color filter layer, at step S320. Thereafter, an upper surface of the overcoating and passivation layer 422 is planarized to improve the planarity thereof, at step S330.

At the fluorescent-excitation-light band-reject-filter layer forming step S340, a fluorescent-excitation-light band-reject-filter layer 423 which blocks a fluorescent-excitation-light-band signal is formed on the planarized upper surface of the overcoating and passivation layer 422.

Thereafter, at step S350, nanoscale oxide or nitride thin films are stacked on top of one another on an upper surface of the fluorescent-excitation-light band-reject-filter layer 423, thus forming an insulation film layer 424.

Figure 4D:
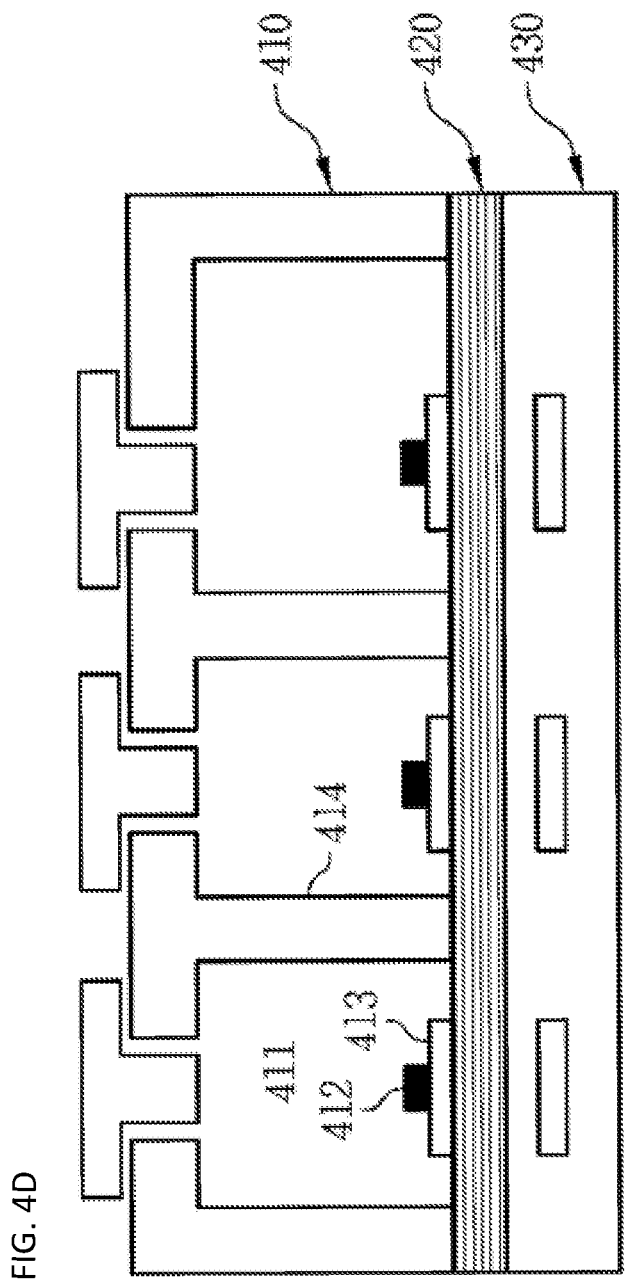

The bio-layer forming step S400 includes forming, on an upper surface of the filter layer 420, a bio-layer 410 which includes light emitting devices 412 and a plurality of reaction regions 411 in each of which a biochemical reaction between a reference sample and a target sample takes place (refer to FIG. 4D).

Preferably, the reaction regions 411 are defined by forming dam-shaped structures 414 on the upper surface of the filter layer 420 and configured such that reception of a reference sample and a target sample in each reaction region 411 can be facilitated and bio-reaction can be induced without the samples being contaminated.

At the bio-layer forming step S400, a light emitting device controller (not shown) for controlling the operation of the light emitting devices and a temperature sensor (not shown) that senses a reaction temperature in each reaction region 411 and thus controls start and finish of the reaction may be installed in the bio-layer 410.

Figure 7:
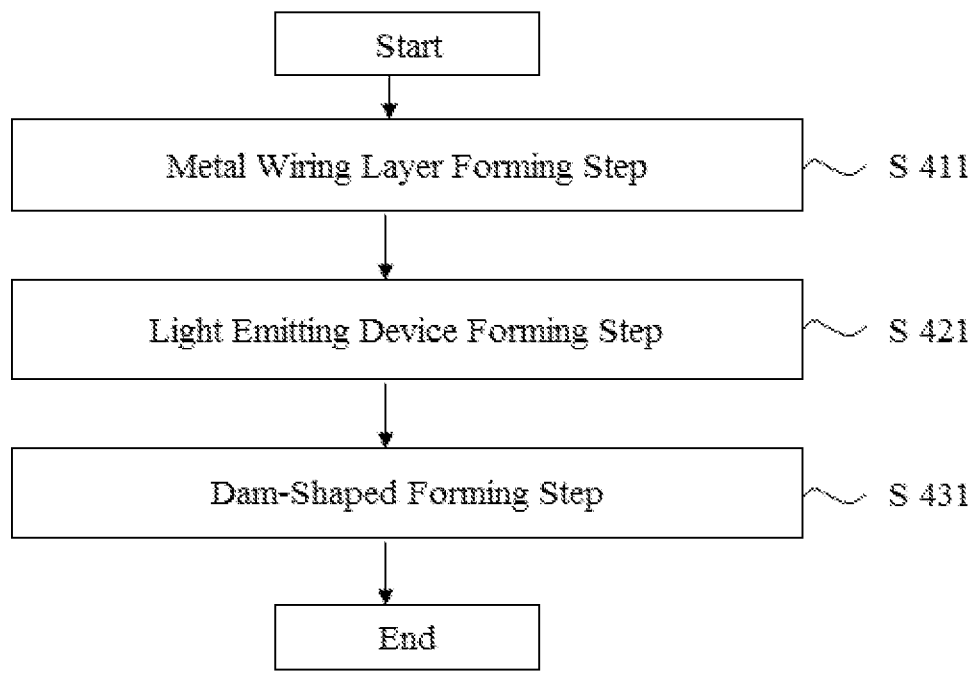
FIG. 7 is a flowchart showing a detailed process of an embodiment of a bio-layer forming step of the biochip manufacturing method according to the present disclosure.

FIG. 7 is a flowchart showing a detailed process of an embodiment of a bio-layer forming step of the biochip manufacturing method according to the present disclosure.

Referring to FIG. 7, the bio-layer forming step according to an embodiment of the present disclosure includes a metal-wiring-layer forming step S411, a light emitting device forming step S421 and a dam-shaped-structure forming step S431.

At the metal-wiring-layer forming step S411, a metal wiring layer for light blocking effect and wiring is formed on the upper surface of the filter layer.

Thereafter, at the light emitting device forming step S421, light emitting devices are provided above the metal wiring layer such that the metal wiring layer can block light emitted from the light emitting devices from being incident on the light sensing units. Furthermore, in the present disclosure, the light emitting devices and the metal wiring layer are disposed vertically above the light sensing unit so that transfer of light from the light emitting devices to the light sensing units can be minimized.

At the dam-shaped-structure forming step S431, the dam-shaped structures are formed on the upper surface of the filter layer such that the reaction regions in each of which a biochemical reaction between a reference sample and a target sample takes place are formed between the dam-shaped structures.

Figure 8:
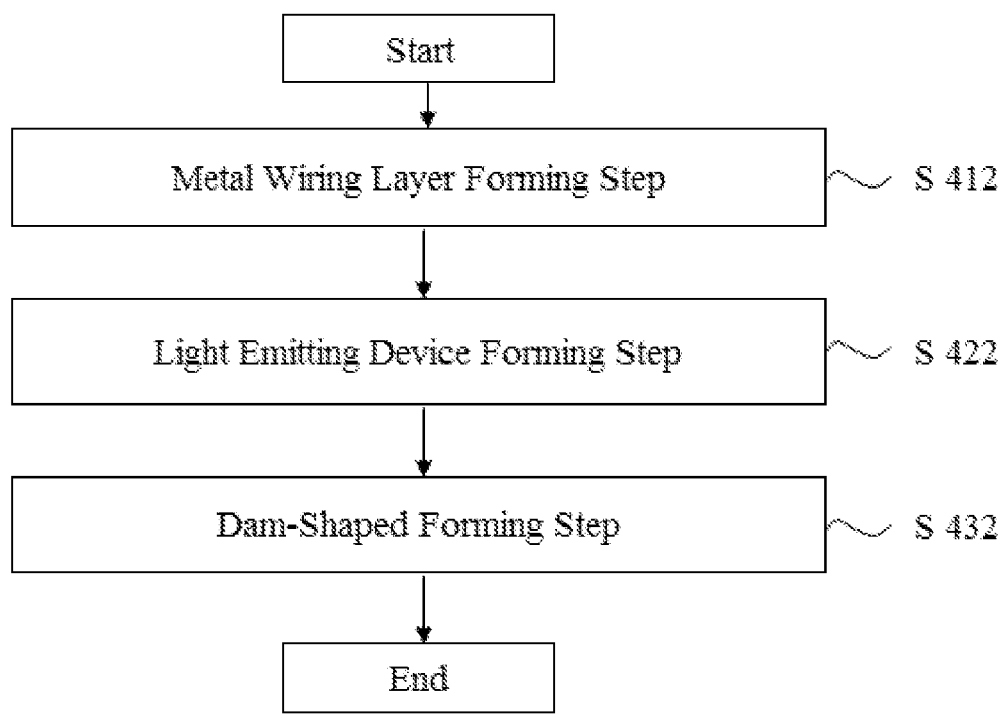
FIG. 8 is a flowchart showing a detailed process of another embodiment of the bio-layer forming step of the biochip manufacturing method according to the present disclosure.

FIG. 8 is a flowchart showing a detailed process of another embodiment of the bio-layer forming step of the biochip manufacturing method according to the present disclosure.

Referring to FIG. 8, the bio-layer forming step according to another embodiment of the present disclosure includes a metal-wiring-layer forming step S412, a light emitting device forming step S422 and a dam-shaped-structure forming step S432.

At the metal-wiring-layer forming step S412, a metal wiring layer for light blocking effect and wiring is formed on the upper surface of the filter layer.

Thereafter, at the light emitting device forming step S422, the light emitting devices are provided above the metal wiring layer such that the metal wiring layer can block light emitted from the light emitting devices from being incident on the light sensing units. Furthermore, in the present disclosure, the light emitting device and the metal wiring layer are disposed vertically above the light sensing units so that transfer of light from the light emitting devices to the light sensing units can be minimized.

At the dam-shaped-structure forming step S432, the dam-shaped structures are formed above the respective light emitting devices such that the reaction regions in each of which a biochemical reaction between a reference sample and a target sample takes place are formed between the dam-shaped structures.

Compared to the bio-layer forming step shown in FIG. 7, the bio-layer forming step shown in FIG. 8 differs from it in that the dam-shaped structures are formed above the respective light emitting devices and the reaction regions are defined between the dam-shaped structures.

Figure 9:
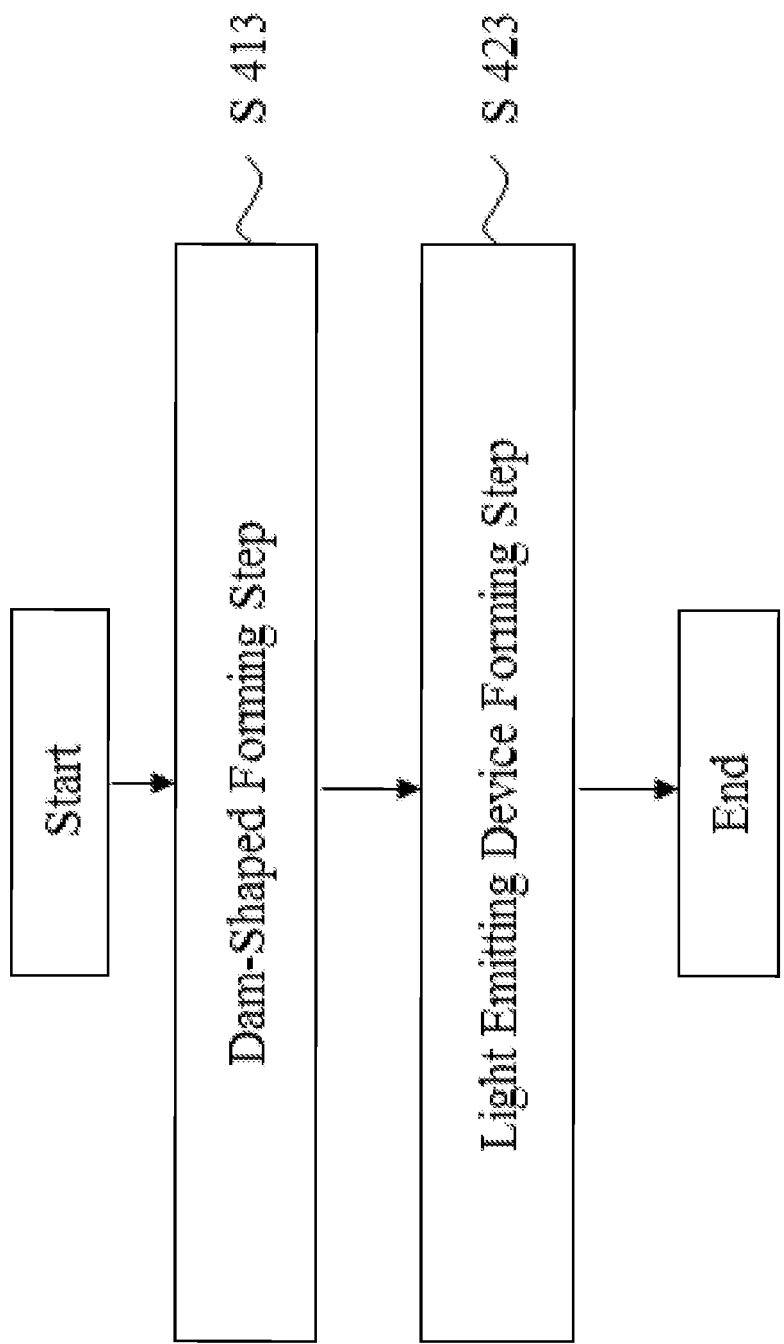
FIG. 9 is a flowchart showing a detailed process of yet another embodiment of the bio-layer forming step of the biochip manufacturing method according to the present disclosure.

FIG. 9 is a flowchart showing a detailed process of yet another embodiment of the bio-layer forming step of the biochip manufacturing method according to the present disclosure.

Referring to FIG. 9, the bio-layer forming step according to yet another embodiment of the present disclosure includes a dam-shaped-structure forming step S413 and a light emitting device forming step S423.

At the dam-shaped-structure forming step S431, the dam-shaped structures are formed on the upper surface of the filter layer such that the reaction regions in each of which a biochemical reaction between a reference sample and a target sample takes place are formed between the dam-shaped structures. In this embodiment, an inner surface of each dam-shaped structure is formed in a lens shape so that light emitted from the corresponding light emitting device can be prevented from being incident on the associated light sensing unit when the light is refracted by and transmitted through the dam-shaped structure having the lens-shaped inner surface.

At the light emitting device forming step S423, the light emitting devices are formed on outer side surfaces of the dam-shaped structures.

The bio-layer forming step according to each of the embodiments of the present disclosure shown in FIGS. 7 through 9 may further include a light-emitting-device coating step of coating the outer surface of each light emitting device to prevent the light emitting device from coming into contact with the reference sample or the target sample in the reaction region and thus prevent a short circuit.

In addition, the bio-layer forming step may further include a reflection-prevention-film forming step of forming a reflection prevention film on the upper surface of the bio-layer to prevent light emitted from the light emitting device from being reflected by the bio-layer.

Figure 10:
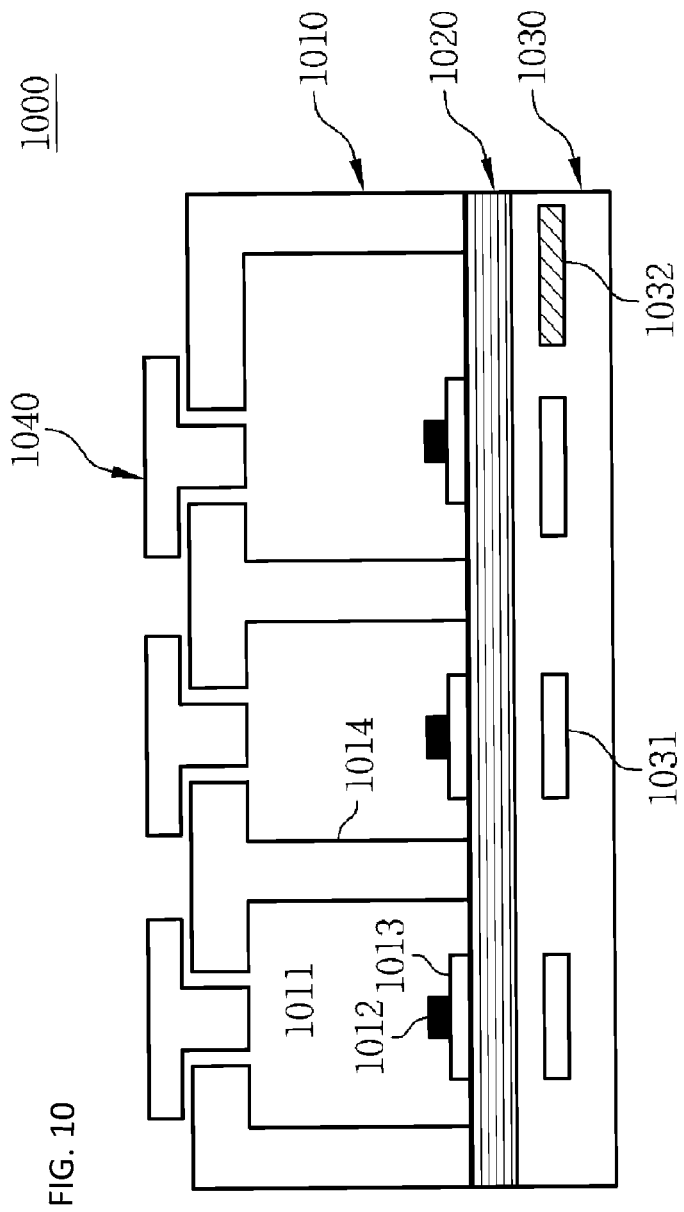
FIG. 10 is a view illustrating the structure of a biochip having improved fluorescent signal sensing properties according to an embodiment of the present disclosure.

FIG. 10 is a view illustrating the configuration of an embodiment of a biochip manufactured by the biochip manufacturing method according to the present disclosure.

Referring to FIG. 10, a biochip 1000 manufactured by the biochip manufacturing method according to the present disclosure includes a bio-layer 1010, a filter layer 1020 and a light sensor layer 1030.

The bio-layer 1010 includes a metal wiring layer 1013 which is formed on an upper surface of the filter layer 1020 and provided for light blocking effect and wiring, light emitting devices 1012 which are provided on upper surface of the metal wiring layer 1013, and dam-shaped structures 1014 which are provided on the upper surface of the filter layer 1020 to form a plurality of reaction regions 1011 in each of which a biochemical reaction between a reference sample and a target sample takes place.

Each of the light emitting devices 1012 is disposed vertically above the corresponding light sensing unit 1031 such that light emitted from the light emitting device 1012 can be prevented from being incident on the light sensing unit 1031.

Although not shown, the bio-layer 101 may further include a light emitting device controller and a temperature sensor.

The reaction regions 1011 each of which has a form of depression are formed in the bio-layer 1010. Each of the reaction regions 1011 is a place where biochemical reaction between a reference sample and a target sample takes place. The biochemical reaction takes place when the target sample is added to the corresponding reaction region 1011 in which the reference sample is disposed.

The reference sample is selected from various types of samples that are able to biochemically react with the target sample. The type of reference sample varies depending on the type of biocheimical reaction intended in the biochip. For example, if the biochemical reaction is an antigen-antibody reaction, the reference sample may be an antigen.

The type of target sample is determined depending on the type of reference sample. For example, if the reference sample is an antigen, the target sample may be blood or the like.

Preferably, the metal wiring layer 1013 is formed under the light emitting device 1012 so that light emitted from the light emitting device 1012 can be prevented from being incident on the corresponding light sensor layer 1030.

The light emitting device emits light of a predetermined wavelength (λ1) and is connected to a light emitting device controller (not shown) that can control on-off switching or the like. The light emitting device is preferably a light emitting diode (LED), which emits light upon application of current and has excellent light emission efficiency.

The metal wiring layer 1013 may be appropriately changed in shape to prevent light emitted from the light emitting device 1012 from being incident on the light sensor layer 1030. For example, the metal wiring layer 1013 may be formed in a form in which it encloses the light emitting device 1012 and is open only toward fluorescent material that remains in the reaction region 1011.

The temperature sensor (not shown) senses the temperature in the reaction region 1011 and thus controls start and finish of reaction.

The filter layer 1020 includes a color filter layer 1021 which is formed on the upper surface of the planarized light sensor layer, an overcoating and passivation layer 1022 which is formed on the upper surface of the color filter layer 1021, a fluorescent-excitation-light band-reject-filter layer 1023 which is formed on the upper surface of the overcoating and passivation layer 1022, and an insulation film layer 1024 which is formed by stacking nanoscale oxide or nitride thin films on the upper surface of the fluorescent-excitation-light band-reject-filter layer 1023.

The filter layer 1020 is disposed between the bio-layer 1010 and the light sensor layer 1030 and functions to prevent light emitted from the light emitting device or light reflected in the reaction region after emitted from the light emitting device from being incident on the light sensor layer 1030.

The filter layer 1020 of the biochip according to the present disclosure is formed by an atomic layer deposition (ALD) method in such a way that sixteen to forty layers of nanoscale thin films such as oxide or nitride films are deposited one by one.

The light sensor layer 1030 is disposed under the filter layer 1020 and includes a plurality of light sensing units 1031.

The light sensing units 1031 are provided on the surface of the light sensor layer 1030 or embedded to a predetermined depth from the surface thereof and function to sense light and to produce an electric charge corresponding to the sensed light. A peripheral circuit (not shown) for producing an electrical signal based on the produced electric charge is connected to each of the light sensing unit 1031. Representative examples of the light sensing units 1031 include charge coupled device (CCD) type image sensors and complementary MOS (CMOS) type image sensors.

The light sensor layer 1030 may further include an image signal processor (1032, hereinafter referred to as an 'ISP') which processes signals generated before and after a fluorescent reaction and thus is able to obtain a signal resulting from the fluorescent reaction.

The ISP 1032 functions process signals reflected by light emitted from the light emitting device before and after a fluorescent reaction and to remove temporal noise which may be generated in pixels. This will be explained in more detail below.

First, a reaction region in which a fluorescent reaction takes place is formed in the bio-layer, and the LED is turned on under the control of the light emitting device controller before the fluorescent reaction is performed.

Here, light emitted from the LED is reflected in the reaction region for fluorescent reaction and then reaches the light sensing unit. The light sensing unit senses a signal reflected in the reaction region and outputs an electrical signal (S1).

While this operation is performed n times, reflected signals are sensed and electrical signals (S1) to (Sn) corresponding to the reflected signals are output. Subsequently, a mean value of the electrical signals is calculated. In this way, a mean value of electrical signals before the reaction is obtained.

This process is conducted in pixels, and a mean value (S_ext) of electrical signals in pixels is obtained and then stored as reference data.

Thereafter, a fluorescent reaction takes place, and a mean value (S_signal) of electrical signals in pixels is obtained again. Data about the mean value (S_signal) is stored.

Here, the obtained mean value (S_signal) is the sum of the mean value (S_ext) of electrical signals obtained before the fluorescent reaction and a mean value (S_fluorescence) of electrical signals resulting from the fluorescent reaction.

Therefore, the signal value (S_fluorescence) resulting from the fluorescent reaction can be calculated by subtracting the signal value (S_ext) obtained before the fluorescent reaction from the signal value (S_signal) obtained after the fluorescent reaction.

As such, after signals are obtained through repetitive measurement, a mean value is calculated by integrating the signals, whereby temporal noise of pixels can be removed. As a result, the sensitivity can be enhanced.

Therefore, preferably, the ISP according to the present disclosure must have a function of integrating signals and be provided with a memory or the like as a storage means for calculating and storing data about integrated signals.

In detail, the ISP may include: a first memory which senses signals reflected by the bio-layer before the fluorescent reaction is performed, integrates the signals, calculates a mean value of electrical signals in pixels, and then stores the mean value; a second memory which senses signals reflected by the bio-layer after the fluorescent reaction is performed, integrates these signals, calculates a mean value of electrical signals in pixels, and then stores the mean value; and a comparison unit which compares the values stored in the first memory and the second memory and thus obtains a signal value resulting from the fluorescent reaction.

Figure 11:
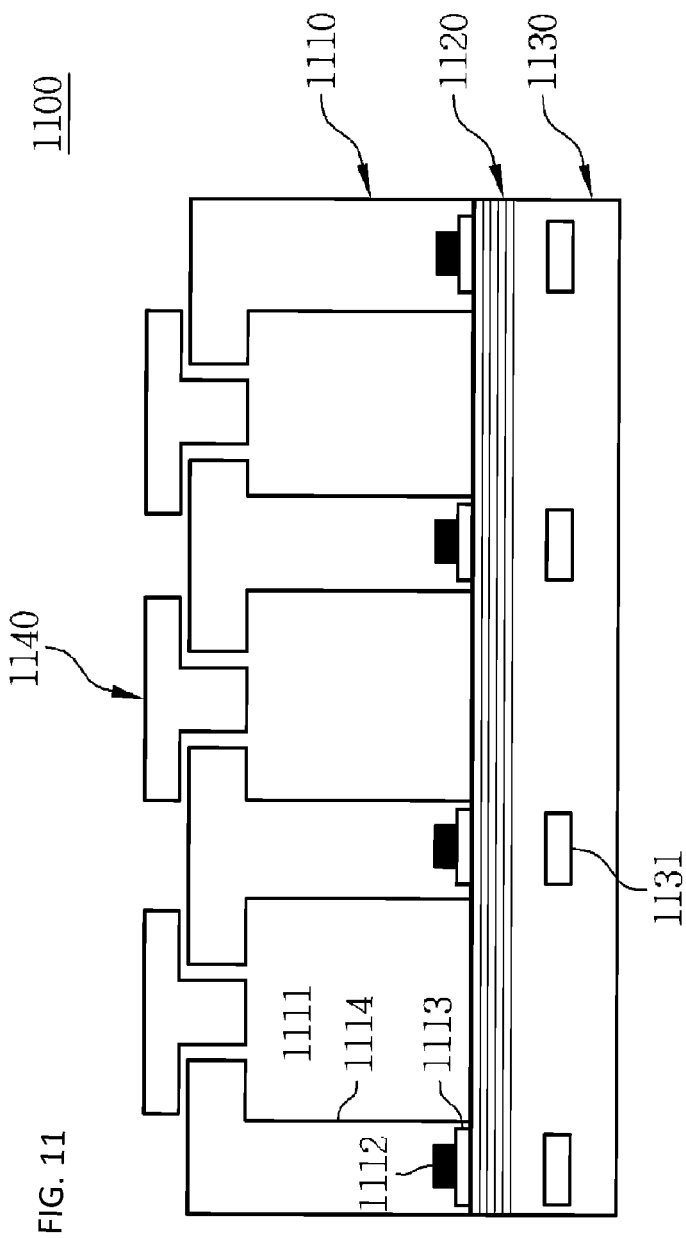
FIG. 11 is a view illustrating the structure of a biochip having improved fluorescent signal sensing properties according to another embodiment of the present disclosure.

FIG. 11 is a view illustrating the configuration of another embodiment of a biochip manufactured by the biochip manufacturing method according to the present disclosure.

Referring to FIG. 11, a biochip 1100 manufactured by the biochip manufacturing method according to the present disclosure includes a bio-layer 1110, a filter layer 1120 and a light sensing layer 1130.

The configurations and functions of the filter layer 1120 and the light sensor layer 1130 are the same as those of the filter layer 1020 and the light sensor layer 1030 illustrated in FIG. 10; therefore, detailed description thereof is deemed unnecessary.

The bio-layer 1110 includes a metal wiring layer 1113 which is formed on the upper surface of the filter layer and provided for light blocking effect and wiring, light emitting devices 1112 which are provided on the upper surface of the metal wiring layer 1113, and dam-shaped structures 1014 which are provided on the respective light emitting devices 1112.

A plurality of reaction regions 1111, in each of which a biochemical reaction between a reference sample and a target sample takes place, are formed between the dam-shaped structures 1114. Each of the light emitting devices 1112 is disposed vertically above the corresponding light sensing unit 1131 such that light emitted from the light emitting device 1112 can be prevented from being incident on the light sensing unit 1131.

Compared to the bio-layer 1010 of FIG. 10, the bio-layer 1110 shown in FIG. 11 differs from it in that the dam-shaped structures 1114 are formed above the respective light emitting devices 1112 and the reaction regions 1111 are formed between the dam-shaped structures 1114.

Figure 12:
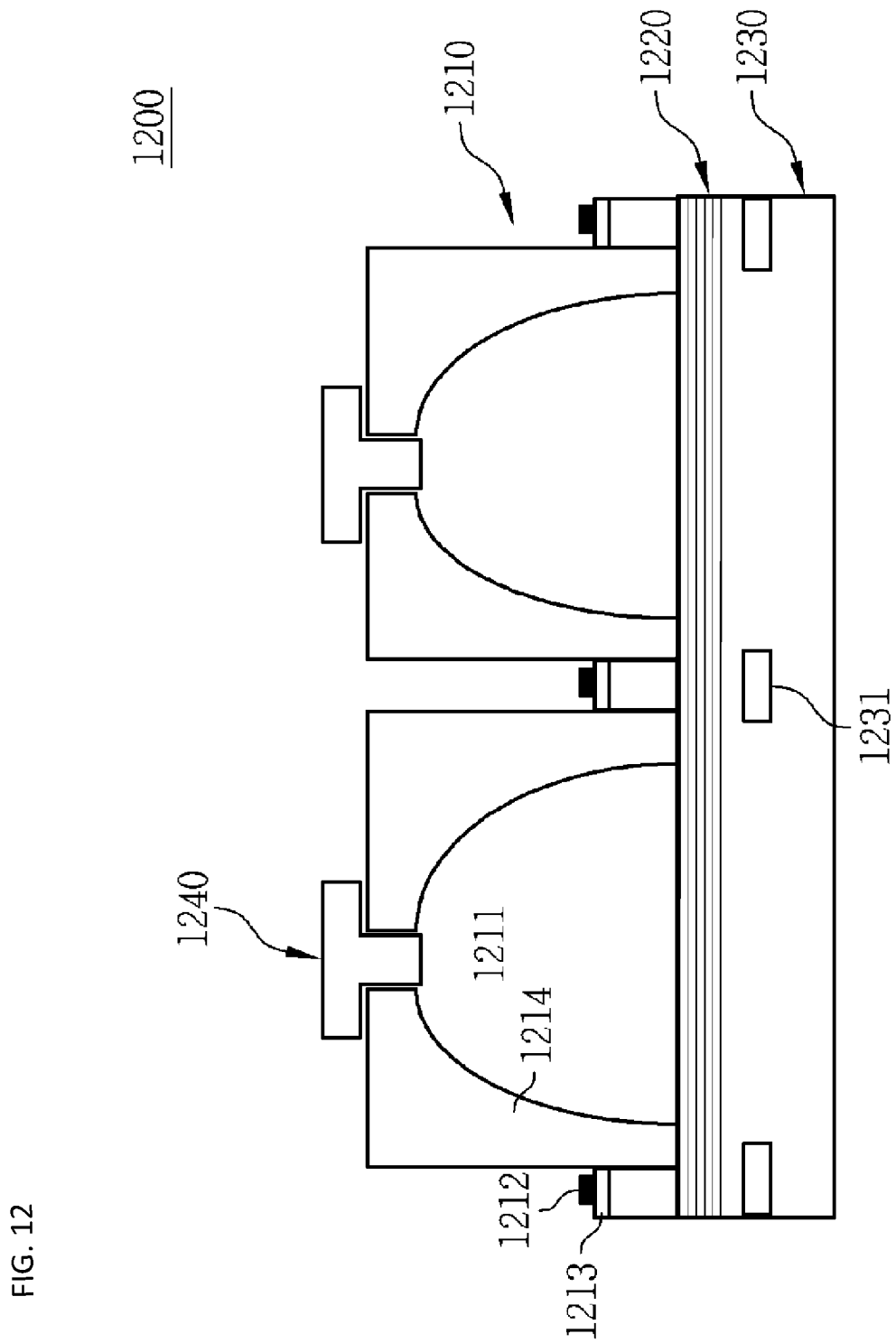
FIG. 12 is a view illustrating the structure of a biochip having improved fluorescent signal sensing properties according to yet another embodiment of the present disclosure.

FIG. 12 is a view illustrating the configuration of yet another embodiment of a biochip manufactured by the biochip manufacturing method according to the present disclosure.

Referring to FIG. 12, a biochip 1200 manufactured by the biochip manufacturing method according to the present disclosure includes a bio-layer 1210, a filter layer 1220 and a light sensing layer 1230.

The configurations and functions of the filter layer 1220 and the light sensor layer 1230 are the same as those of the filter layer 1020 and the light sensor layer 1030 illustrated in FIG. 10; therefore, detailed description thereof is deemed unnecessary.

The bio-layer 1210 includes the dam-shaped structures 1214 which are provided on the upper surface of the filter layer 1220 to form a plurality of reaction regions 1211 in each of which a biochemical reaction between a reference sample and a target sample takes place, and light emitting devices 1212 which are provided on outer side surfaces of the dam-shaped structures 1214.

In this embodiment, an inner surface of each dam-shaped structure 1214 has a lens shape so that light emitted from the corresponding light emitting device 1212 can be prevented from being incident on the associated light sensing unit after being reflected by the dam-shaped structure 1214 having the lens-shaped inner surface.

Figure 13:
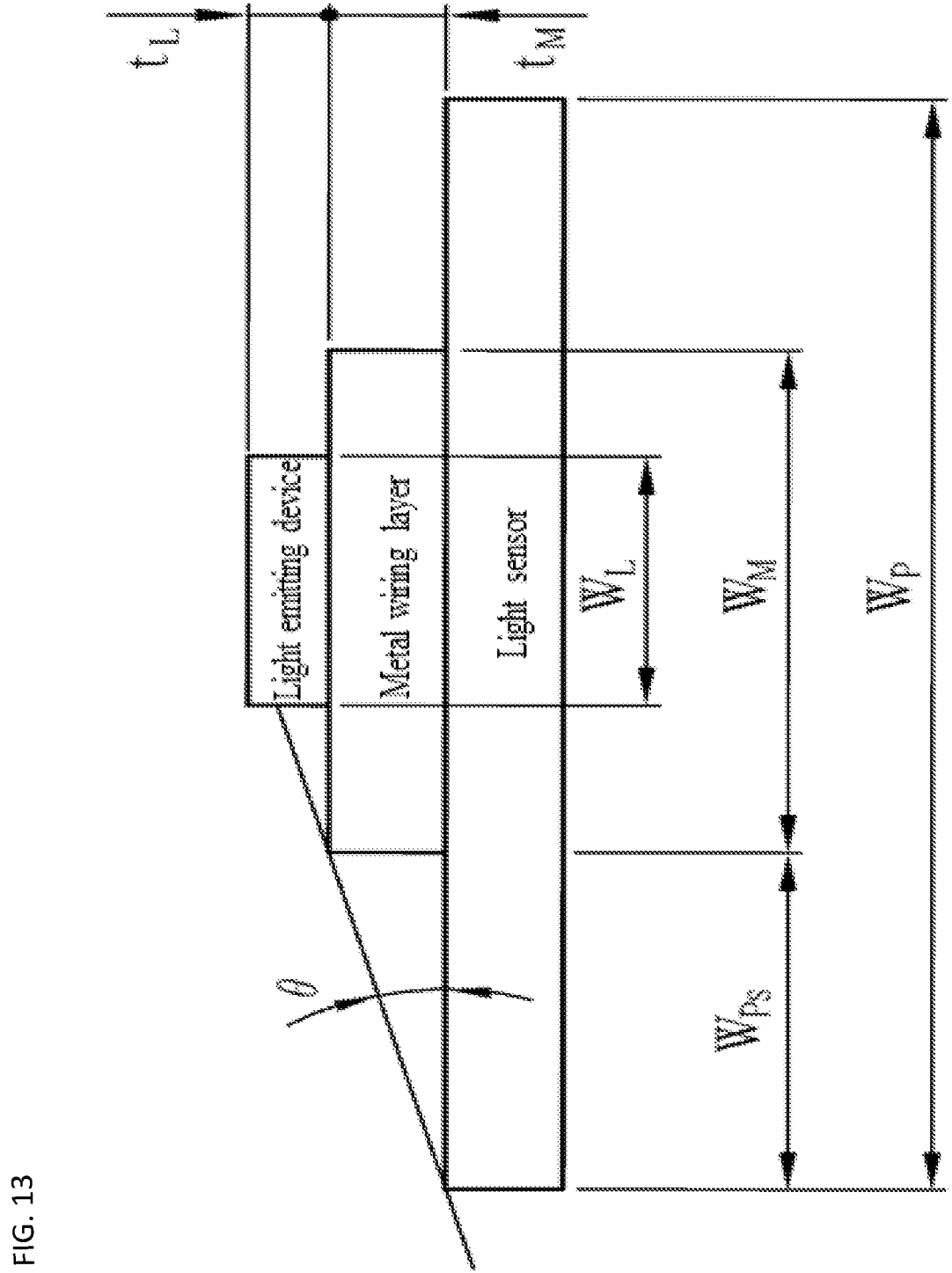
FIG. 13 is a view relationship in thickness and width of a light emitting device and a metal wiring layer of the biochip according to the present disclosure.

FIG. 13 is a view relationship in thickness and width between the light emitting device and the metal wiring layer of the biochip having improved fluorescent signal sensing properties according to the present disclosure.

As shown in FIG. 13, the thicknesses and the lengths of the light emitting device and the metal wiring layer and the length of the light sensing unit of the biochip according to the present disclosure are determined by the following equations.

$$\tan \theta = t_L \times (W_M - W_L)/2$$

$$W_{PS} = t_M/\tan \theta$$

$$W_P = 2W_{PS} + W_M$$

Here, θ denotes an angle between the upper surface of the light sensing unit and a linear connecting an edge of the upper surface of the light emitting device, the corresponding edge of the upper surface of the metal wiring layer and the corresponding edge of the upper surface of the light sensing unit. $t_L$ denotes the thickness of the light emitting device. $t_M$ denotes the thickness of the metal wiring layer. $W_L$ denotes the length of the light emitting device. $W_M$ denotes the length of the metal wiring layer. $W_P$ denotes the length of the light sensing unit. $W_{PS}$ denotes the length of a portion of the upper surface of the light sensing unit above which the metal wiring layer is not present.

Figure 14:
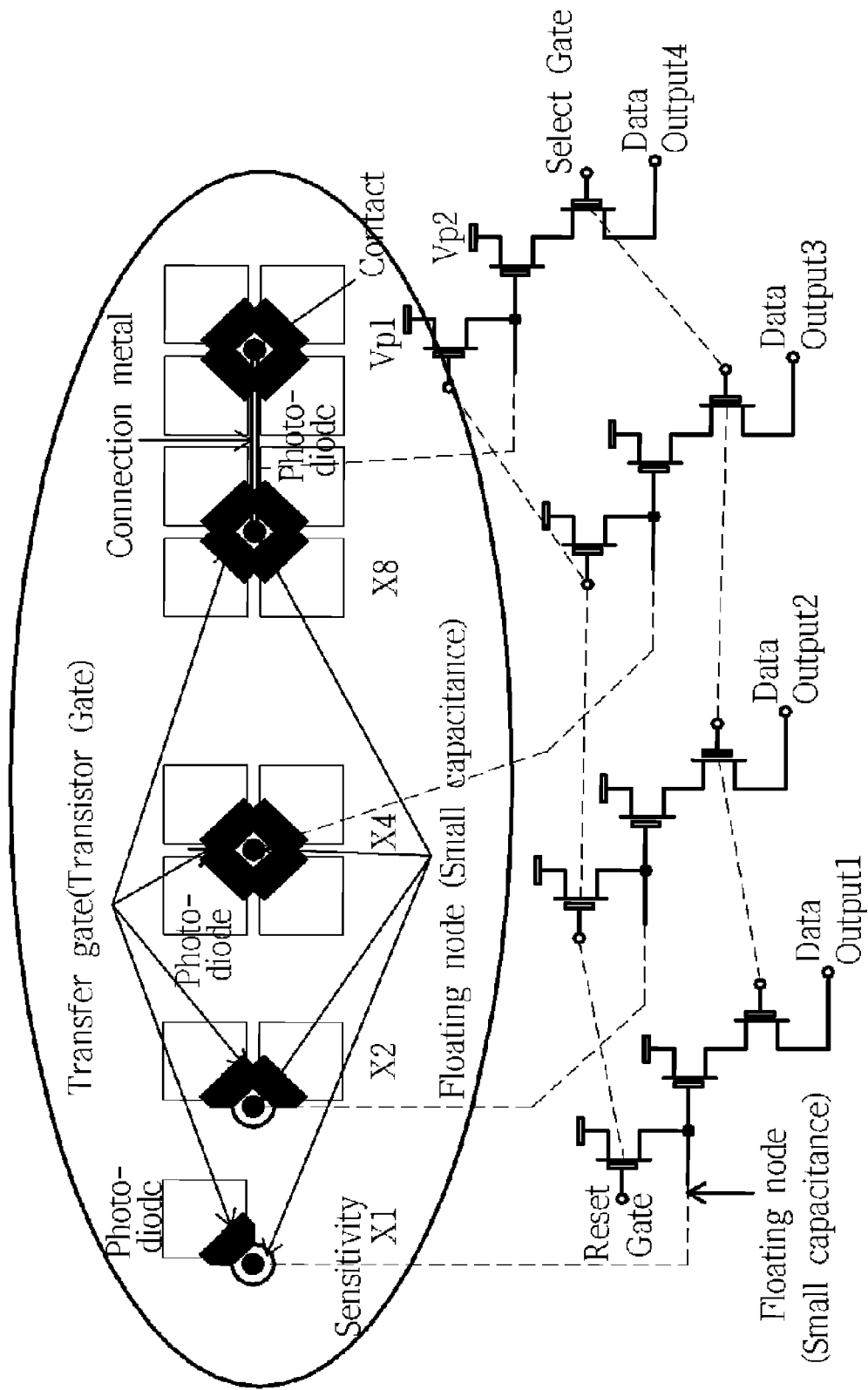
FIG. 14 is a view illustrating the configuration of a light sensing unit of the biochip according to the present disclosure.

FIG. 14 is a view illustrating the configuration of a light sensing unit of the biochip having improved fluorescent signal sensing properties according to the present disclosure.

The light sensing units are provided in the light sensor layer. Preferably, a photodiode is used as each light sensing unit. Furthermore, in the biochip having improved fluorescent signal sensing properties according to the present disclosure, so as to ensure reliable operation of the system and increase a sensing range, as shown in FIG. 14, unit photodiodes having the same size may be arranged or, more preferably, a light sensing unit which has a repetitive array of photodiodes having sizes integer times that of the unit photodiodes may be used.

Figure 15:
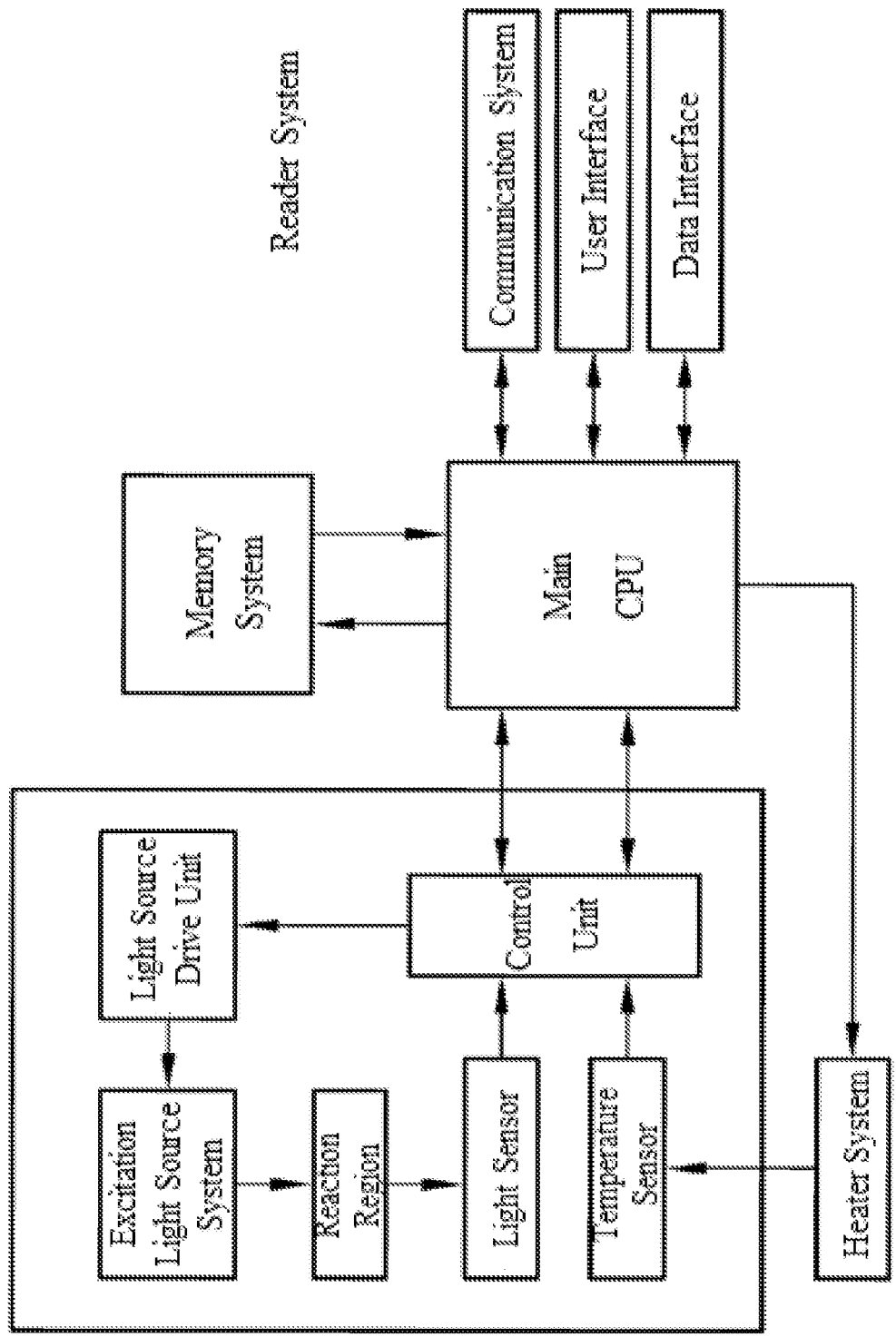
FIG. 15 is a view illustrating a system using the biochip according to the present disclosure.

FIG. 15 is a view illustrating a system using the biochip having improved fluorescent signal sensing properties according to the present disclosure.

A molecular diagnosis kit including the biochip according to the present disclosure requires a reader system: which makes a pair with the kit and compensates for individual deviation of each kit; which operates the kit and peripheral environments such that they are suitable for a reaction system of biochemical materials used for molecular diagnosis; which controls the temperature, etc. in response to each operation; and which collects, analyzes and processes sensing data obtained from the kit and produces final molecular diagnosis results.

The molecular diagnosis kit including the biochip according to the present disclosure is connected to the reader system by a main control unit (MCU) and functions to obtain stable and available signals through a process of: processing sensing measurement results; removing various types of noises caused during the sensing process to extract pure signals; and integrating the pure signals.

Figure 16:
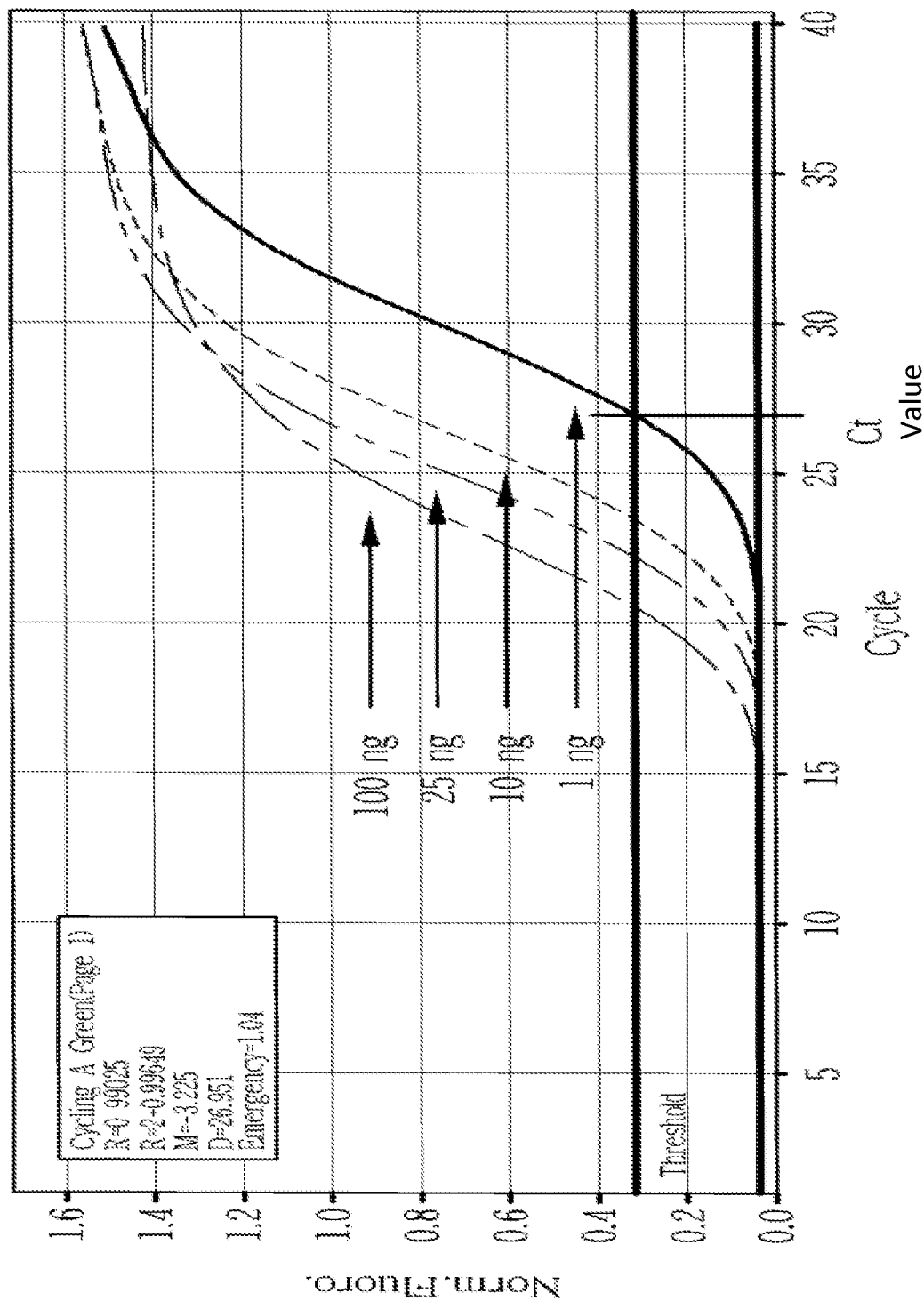
FIG. 16 is a view illustrating a method of conducting a real time quantitative PCR (polymer chain reaction) using the system with the biochip according to the present disclosure.

FIG. 16 is a view illustrating a method of conducting a real time quantitative PCR (polymer chain reaction) using the system with the biochip according to the present disclosure.

The conventional PCR method is a method of performing an electrophoretic test to check amplified DNA after the PCR and determining whether target DNA is present in a target sample through checking whether the target DNA has been amplified. However, in this conventional method, it is impossible to determine the amount of target DNA before the PCR.

The real time quantitative PCR refers to a method in which amplification in the amount of DNA resulting from the thermal cycle of PCR is measured in real time through fluorescence. As the cycle proceeds, the amount of fluorescence is increased, and in response to this, a graph is formed. However, depending on an initial amount of DNA, a point (Ct value) to which the graph exponentially increases is varied. After a PCR standard curve is obtained from a standard sample, a PCR Ct value of an unknown sample is applied to the standard curve and guantified. In the present disclosure, the real time quantitative PCR is possible.

Meanwhile, the present disclosure has a location-based multiplexed molecular diagnosis function.

The term "multiplexed molecular diagnostics" refers to a method in which multiple kinds of target DNA are detected when molecular diagnosis (typically, PCR diagnosis) is conducted. For example, there are several kinds of bacterium inducing tuberculosis. Thus, when a suspected tuberculosis patient is tested for tuberculosis, there is the need for checking the kinds of bacterium that induces the tuberculosis of the patient. In this case, a method of detecting several kinds of target DNA through a single PCR process is preferably used. This method is called multiplexed molecular diagnostics.

As such, the multiplexed molecular diagnostics is a method in which a single PCR tube into which PCR reagent and a sample obtained from the patient are put is only used to detect several kinds of target DNA. For this, different colors of fluorescent materials are used, and detected several kinds of target DNA are distinguished from each other by wavelength bands of fluorescence. However, this method can typically detect only six or less kinds of DNA.

A DNA microarray method is another method for conducting the quantitative PCR. This method includes applying target DNA and complementary DNA (DNA probe) on the surface of a substrate, and then determining whether target DNA is present or not by means of checking whether target DNA has been coupled to the DNA probe.

Although this method can detect a large number of kinds of target DNA, there are problems in that, after the PCR has been performed, amplified DNA must be applied to a microarray, and several steps are required to obtain a result of the PCR, so that it takes a lot of time to obtain the result.

The location-based multiplexed molecular diagnosis method according to the present disclosure is a notion similar to that of the DNA microarray method. That is, because a user knows the locations of DNA probes in advance, it can be appreciated that if fluorescence is generated from a location, a corresponding kind of target DNA is present. However, unlike the DNA microarray method, the present disclosure is configured such that the PCR and a DNA detection operation can be combined with each other and thus is advantageous in that the PCR and the DNA detection process can be performed in a single place and the time it takes to perform the detection process can be reduced.

Figure 17A:
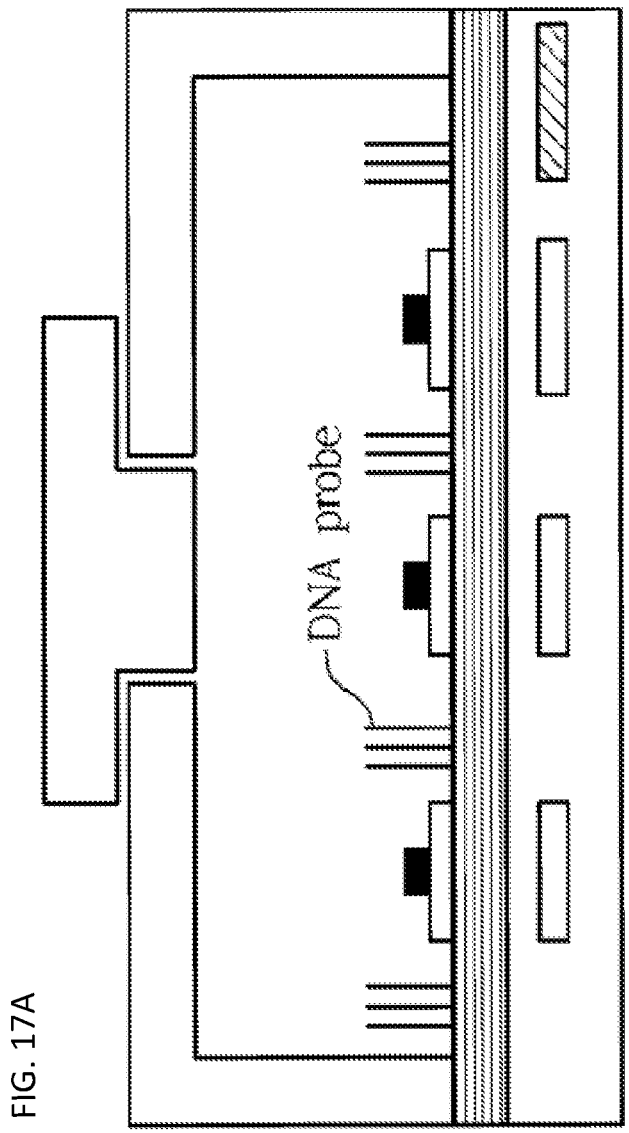
FIGS. 17A and 17B are views illustrating a method of conducting a location-based multiplexed diagnosis in a DNA microarray manner using the biochip according to the present disclosure.
Figure 17B:
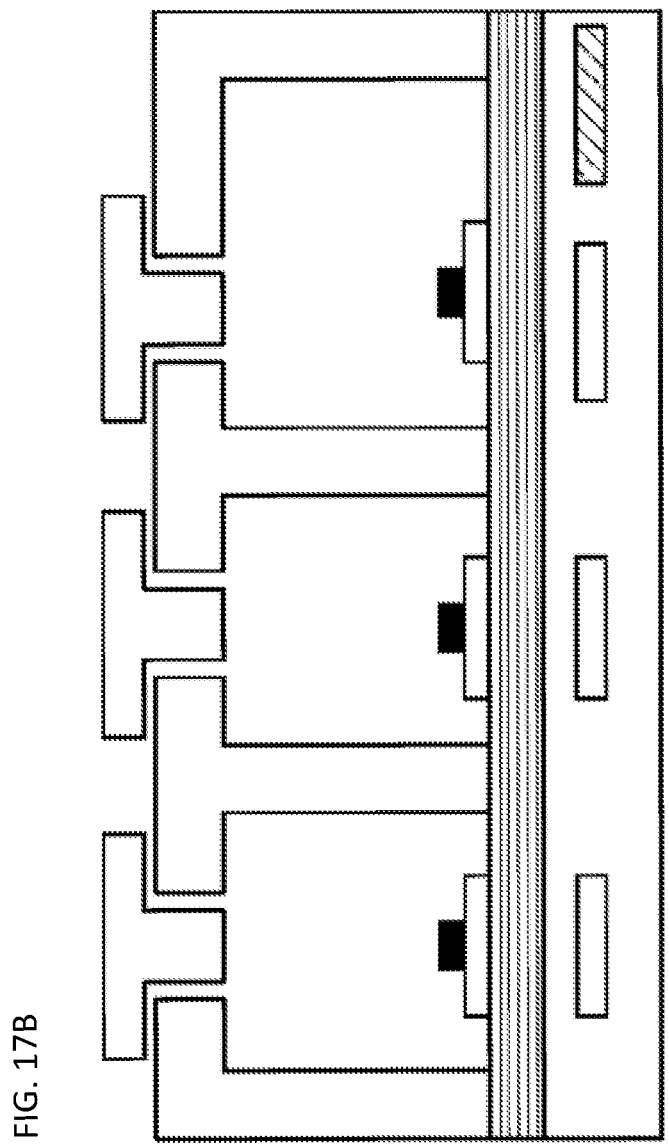

FIGS. 17A and 17B are views illustrating a method of conducting location-based multiplexed diagnosis in a DNA microarray manner using the biochip according to the present disclosure.

FIG. 17A is a view illustrating a method of detecting several kinds of target DNA from different locations in a single PCR reaction chamber in the case where the locations of DNA probes are known. FIG. 17B is a view illustrating a method of using a plurality of PCR reaction chambers and detecting several kinds of target DNA from respective different chambers.

In a method for manufacturing a biochip having improved fluorescent signal sensing properties and a biochip manufactured by the method according to the present disclosure, a metal wiring layer and a filter layer for fluorescent excitation light are provided between a bio-layer and a light sensor layer. Thereby, noise caused from fluorescent excitation light during a bio-reaction process can be minimized. As a result, minute-fluorescent-signal sensing performance in the light sensor layer can be enhanced.

Furthermore, a fluorescent sensor having an improved minute-fluorescent-signal sensing function, and a bio-LOC (lab on a chip) including a bio reaction region having a location-based multiplexed function are suitable for application of fluorescence-based real-time quantitative PCR, whereby time and cost required to perform quantitative molecular diagnosis can be reduced. In addition, industrially, the present disclosure makes it possible to embody various industrial models in biomedical markets.

While exemplary embodiments of the present disclosure have been described above, it will be understood to those skilled in the art that the embodiments described are by way of example only. Accordingly, the disclosure described herein should not be limited based on the described embodiments. Furthermore, those skilled in the art will appreciate that various modifications and changes are possible without departing from the technical spirit of the present disclosure.

What is claimed is:

1. A biochip having improved fluorescent signal sensing properties, comprising:
   a bio-layer embedded with light emitting devices each of which has a metal wiring layer lying thereunder, and formed with a plurality of reaction regions each of which a biochemical reaction between a reference sample and a target sample to take place;
   a filter layer formed under the bio-layer; and
   a light sensor layer which is formed under the filter layer, and in which a plurality of light sensing units are formed,
   wherein the filter layer is formed by planarizing an upper portion of the light sensor layer and stacking nanoscale thin films through an atomic layer deposition (ALD) process, and light emitted from each of the light emitting devices is blocked from being incident on the corresponding light sensing unit,
   wherein the light sensor layer further comprises:
      an image signal processor configured for analyzing and processing a signal output from the bio-layer, and
   wherein the filter layer comprises:
      a color filter layer formed over the planarized light sensor layer;
      an overcoating and passivation layer formed over the color filter layer; a fluorescent-excitation-light band-reject-filter layer formed over the overcoating and passivation layer; and
      an insulation film layer formed by stacking nanoscale oxide or nitride thin films over the fluorescent-excitation-light hand-reject-filter layer.

2. The biochip according to claim 1, further comprising, in the bio-layer:
   a light emitting device controller configured for controlling operation of the light emitting devices; and
   a temperature sensor configured for sensing a temperature in each of the reaction regions and controlling start and finish of a bio-reaction.

3. The biochip according to claim 1, wherein the image signal processor comprises:
   a first memory which is configured to sense signals reflected by the bio-layer before a fluorescent reaction is performed, integrate the signals, calculate a mean value of electrical signals in pixels, and then store the mean value;
   a second memory which is configured to sense signals reflected by the bio-layer after the fluorescent reaction is performed, integrate the signals, calculate a mean value of electrical signals in pixels, and then store the mean value; and
   a comparison unit which is configured to compare the mean values stored in the first memory and the second memory and thus obtain a signal value resulting from the fluorescent reaction, wherein the image signal processor is configured to remove temporal noise in pixels and thus enhance sensitivity.

4. The biochip according to claim 1, wherein the bio-layer comprises:
   the metal wiring layer formed over the filter layer and provided for light blocking and wiring;
   the light emitting devices provided over the metal wiring layer; and
   dam-shaped structures formed on the upper surface of the filter layer to form the plurality of reaction regions each of which is configured for the biochemical reaction between the reference sample and the target sample to take place, wherein the light emitting devices are formed vertically over the respective light sensing units so that light emitted from each of the light emitting devices is blocked from being incident on the corresponding light sensing unit.

5. The biochip according to claim 1, wherein the bio-layer comprises:
the metal wiring layer formed over the filter layer and provided for light blocking and wiring;
the light emitting devices formed over the metal wiring layer; and
dam-shaped structures formed over the light emitting devices,
wherein the plurality of reaction regions, each of which is configured for the biochemical reaction between the reference sample and the target sample to take place, are formed between the dam-shaped structures, and the light emitting devices are formed vertically over the light sensing units so that light emitted from each of the light emitting devices is blocked from being incident on the corresponding light sensing unit.

6. The biochip according to claim 1, wherein the bio-layer comprises:
dam-shaped structures formed on the upper surface of the filter layer to form the plurality of reaction regions in each of which the biochemical reaction between the reference sample and the target sample takes place; and
light emitting devices formed on outer side surfaces of the dam-shaped structures,
wherein an inner surface of each of the dam-shaped structures is formed in a lens shape so that light emitted from each of the light emitting devices is prevented from being reflected by the dam-shaped structure and being incident on the corresponding light sensing unit.

7. The biochip according to claim 4, wherein each of the dam-shaped structures is made of at least one selected from among silicone (Si), glass, plastic, sapphire, photoresist, diamond, grapheme and metal.

8. The biochip according to claim 4, further comprising:
an isolation cover covering the dam-shaped structures and isolating the reaction regions.

9. The biochip according to claim 4, wherein thicknesses and lengths of each of the light emitting devices and the metal wiring layer and the length of the associated light sensing unit are determined by following equations, $$\tan \theta = t_L \times (W_M - W_L)/2$$

$$W_{PS} = t_M / \tan \theta$$

$$W_P = 2W_{PS} + W_M$$

where,
$\theta$ denotes an angle between an upper surface of the light sensing unit and a linear connecting an edge of an upper surface of the light emitting device, a corresponding edge of an upper surface of the metal wiring layer and a corresponding edge of an upper surface of the light sensing unit, $t_L$ denotes a thickness of the light emitting device, $t_M$ denotes a thickness of the metal wiring layer, $W_L$ denotes a length of the light emitting device, $W_M$ denotes a length of the metal wiring layer, $W_P$ denotes a length of the light sensing unit, $W_{PS}$ denotes a length of a portion of the upper surface of the light sensing unit above which the metal wiring layer is not present.

10. The biochip according to claim 1, wherein the light sensing units comprise:
unit photodiodes having a same size, or a repetitive array of photodiodes having sizes integer times the size of the unit photodiodes.

* * * * *